(12) United States Patent
Greenly

(10) Patent No.: US 10,201,202 B2
(45) Date of Patent: Feb. 12, 2019

(54) WEARABLE DISEASE PREVENTION DEVICE

(71) Applicant: No Touch L. L. C., St. Paul, MN (US)

(72) Inventor: Boone Lee Greenly, St. Paul, MN (US)

(73) Assignee: No Touch L.L.C., St. Paul, MN (US)

( * ) Notice: Subject to any disclaimer, the term of this patent is extended or adjusted under 35 U.S.C. 154(b) by 0 days.

(21) Appl. No.: 15/653,883

(22) Filed: Jul. 19, 2017

(65) Prior Publication Data

US 2018/0027908 A1    Feb. 1, 2018

Related U.S. Application Data

(60) Provisional application No. 62/368,747, filed on Jul. 29, 2016.

(51) Int. Cl.
| | |
|---|---|
| G08B 23/00 | (2006.01) |
| A41D 31/00 | (2006.01) |
| A61B 5/00 | (2006.01) |
| H01F 7/20 | (2006.01) |
| A61B 5/11 | (2006.01) |
| H01F 7/02 | (2006.01) |

(52) U.S. Cl.
CPC ........ A41D 31/0011 (2013.01); A61B 5/1116 (2013.01); A61B 5/486 (2013.01); A61B 5/4833 (2013.01); A61B 5/681 (2013.01); A61B 5/6805 (2013.01); A61B 5/6823 (2013.01); A61B 5/6826 (2013.01); A61B 5/6844 (2013.01); A61B 5/746 (2013.01); H01F 7/20 (2013.01); H01F 7/0294 (2013.01)

(58) Field of Classification Search
CPC ... A41D 31/0011; A61B 5/486; A61B 5/1116; A61B 5/4833; A61B 5/6805; A61B 5/681; A61B 5/6823; A61B 5/6826; A61B 5/6844; A61B 5/746; H01F 7/20; H01F 7/0294
USPC ...................................................... 340/573.1
See application file for complete search history.

(56) References Cited

U.S. PATENT DOCUMENTS

| | | |
|---|---|---|
| 1,772,601 A | 1/1929 | Dunham |
| 4,178,589 A | 12/1979 | Nunn et al. |
| 4,692,748 A | 9/1987 | Pinsak et al. |
| 4,965,553 A | 10/1990 | DelBiondo, II et al. |

(Continued)

FOREIGN PATENT DOCUMENTS

CA    2426976 A1    10/2004

OTHER PUBLICATIONS

"Lumo Lift Posture Coach," Lumo, retrieved from internet www.lumobodytech.com, Dec. 2013, 5 pp.

(Continued)

*Primary Examiner* — Zhen Y Wu
(74) *Attorney, Agent, or Firm* — Grumbles Law PLLC; Brittany Nanzig

(57) ABSTRACT

A wearable device for preventing the spread of disease by detecting when a wearer's hand comes into close proximity of the wearer's face. The device can preferably issue an immediate warning to the wearer to prevent contact between the wearer's hand and face and to change a wearer's face-touching habit in order to prevent future occurrences. More specifically, the device can be comprised of a housing, a backer, magnets to attach the backer to the housing, a signal emitter, a plurality of sensors, a micro USB charge port, and a power button.

18 Claims, 5 Drawing Sheets

(56) References Cited

U.S. PATENT DOCUMENTS

| | | | |
|---|---|---|---|
| 5,578,066 A | 11/1996 | Gober | |
| 5,590,421 A | 1/1997 | Craner | |
| 7,315,249 B2 | 1/2008 | Littell | |
| 7,476,102 B2 | 1/2009 | Maples | |
| 8,533,620 B2 | 9/2013 | Hoffman et al. | |
| 8,585,588 B2 | 11/2013 | Kovarik et al. | |
| 9,721,450 B2 * | 8/2017 | Kumar | G08B 21/0407 |
| 2004/0027247 A1 * | 2/2004 | Pittman | A61F 5/50 |
| | | | 340/573.7 |
| 2004/0160326 A1 * | 8/2004 | Zarouri | G08B 21/18 |
| | | | 340/573.1 |
| 2006/0219251 A1 | 10/2006 | Ray | |
| 2007/0028341 A1 | 2/2007 | Smith | |
| 2010/0308089 A1 * | 12/2010 | Chien | A45F 5/00 |
| | | | 224/183 |
| 2012/0245498 A1 * | 9/2012 | Krenzel | A61F 5/3738 |
| | | | 602/4 |
| 2015/0049037 A1 | 2/2015 | Vincent et al. | |
| 2015/0102208 A1 * | 4/2015 | Appelboom | G06F 19/3481 |
| | | | 250/208.2 |
| 2015/0116920 A1 * | 4/2015 | Franklin | G06F 1/1626 |
| | | | 361/679.26 |
| 2015/0289822 A1 * | 10/2015 | Dugan | A61B 5/1075 |
| | | | 600/301 |
| 2015/0320340 A1 | 11/2015 | Verma | |
| 2016/0074205 A1 * | 3/2016 | Yao | A61F 5/3738 |
| | | | 602/4 |
| 2017/0019642 A1 * | 1/2017 | Mai | G06F 1/266 |
| 2018/0027908 A1 * | 2/2018 | Greenly | A41D 31/0011 |

OTHER PUBLICATIONS

"Upright Go, Fix Your Screen-Slouch, Correct Your Posture by Upright Technologies," www.kickstarter.com, retrieved from Internet www.kickstarter.com, Aug. 2017, 27 pp.

Xu et al., "A Real-Time Hand Detection System during Hand over Face Occlusion," International Journal of Multimedia and Ubiquitous Engineering, v. 10, n. 8, Aug. 2015, pp. 287-302.

* cited by examiner

WEARABLE DISEASE PREVENTION DEVICE

CROSS-REFERENCE TO RELATED APPLICATION

This application claims the benefit of U.S. Provisional Application No. 62/368,747 filed Jul. 29, 2016 and titled WEARABLE DISEASE PREVENTION DEVICE.

FIELD OF THE INVENTION

This disclosure relates to a device that can be worn and that prevents the spread of disease. More specifically, it relates to a device that can detect when a wearer's hand comes into close proximity of the wearer's face and that can issue a warning to the wearer to prevent contact between the wearer's hand and face.

BACKGROUND OF THE INVENTION

The spread of disease via infection is a process that has accompanied humans and other social species for their entire existence. There are three main components to the chain of infection: a source of germs, a means of transmission, and a susceptible host. In order to break the chain of infection, one of these three main components must be compromised. Because germs are commonly found on individuals' hands, and individuals touch hundreds of objects every day, hands are often seen as a source of germs and a means of transmission. For example, cold and flu are transmitted from direct human-to-human contact, such as touching or droplets (i.e., sneezing), or indirect contact such as through touching of the same surface.

Currently, workers at hospitals and health care institutions wash their hands and use hand sanitizer to attempt to break the chain of infection. However, even after these workers wash their hands, they continue to touch surfaces and objects capable of keeping germs alive long enough to be transferred to a new, susceptible host. Therefore, attempts to block the source of germs by hand washing and hand sanitizer have not succeeded in breaking the chain of infection, and a new method of disease prevention is needed.

One solution to the above-referenced problem is for individuals to refrain from touching their faces. By refraining from touching eyes, nose, and lips, a person effectively prevents disease transmission. However, individuals unconsciously touch their faces hundreds of times per day. Therefore, a system is needed that aids individuals in reducing facial touching in order to diminish disease transmission.

SUMMARY OF THE INVENTION

The present disclosure relates to a device that prevents the spread of disease by encouraging individuals to refrain from touching their faces with their hands. More specifically, the disclosed invention is comprised of a wearable device that alerts a wearer when his or her hand or hands comes into close proximity with his or her face.

DETAILED DESCRIPTION

Figure 1:
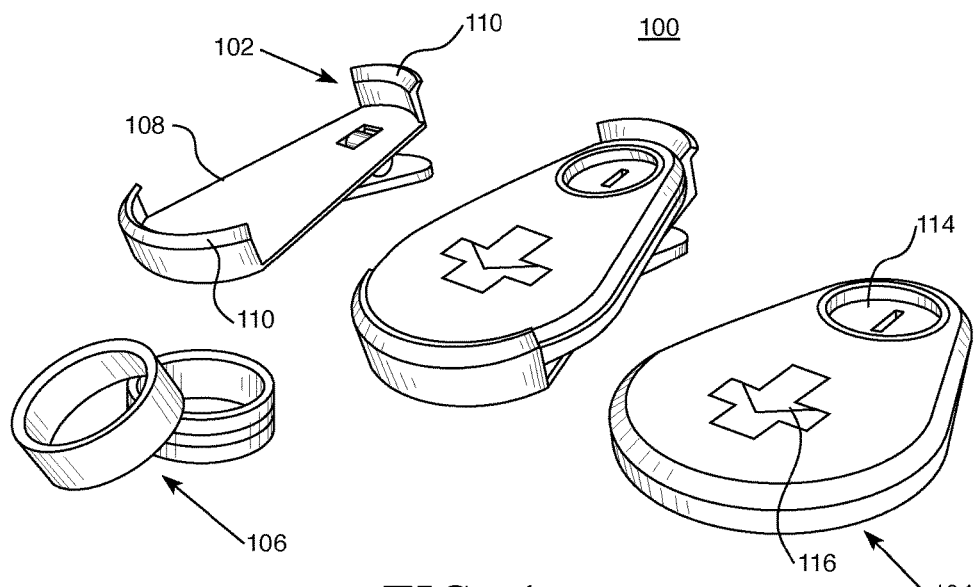
FIG. 1 is a perspective view of a wearable disease prevention device according to a first embodiment of the present invention.

The present disclosure relates to a wearable disease prevention device that is used to prevent the spread of disease by detecting facial touching. Various embodiments of the wearable disease prevention device will be described in detail with reference to the drawings, wherein like reference numerals represent like parts and assemblies throughout the several views. Reference to various embodiments does not limit the scope of the wearable disease prevention device disclosed herein. Additionally, any examples set forth in this specification are not intended to be limiting and merely set forth some of the many possible embodiments for the wearable disease prevention device. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

Some embodiments of the wearable disease prevention device disclosed herein include features that detect, warn, and/or track facial touching by an individual. The features are designed to discourage wearers of the device from touching their own faces with their hands, which are likely covered in unwanted bacteria or viruses. Therefore, the device can prevent contraction and the spread of disease.

Figure 2:
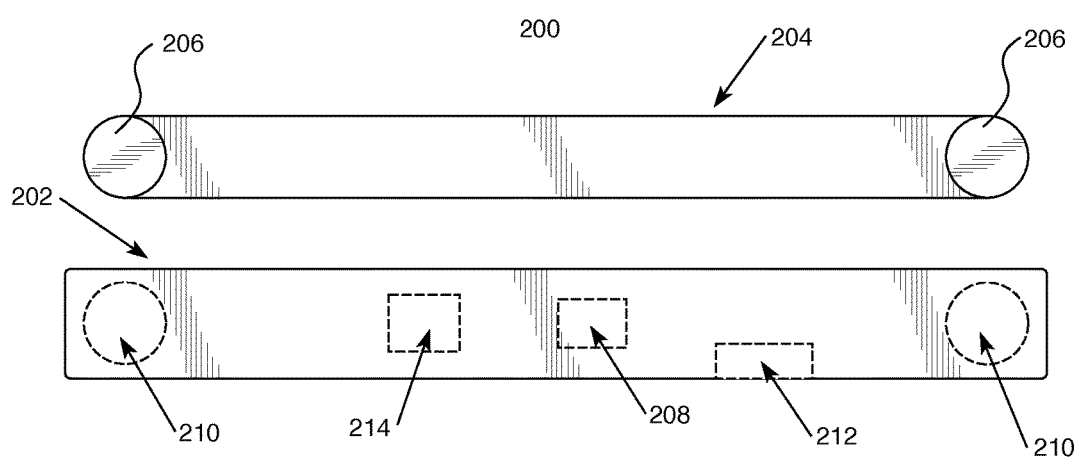
FIG. 2 is plan top view of a wearable disease prevention device according to a second embodiment of the present invention.
Figure 3:
FIG. 3 illustrates one location where the wearable disease prevention device of FIG. 1 can be attached on a user.
Figure 4:
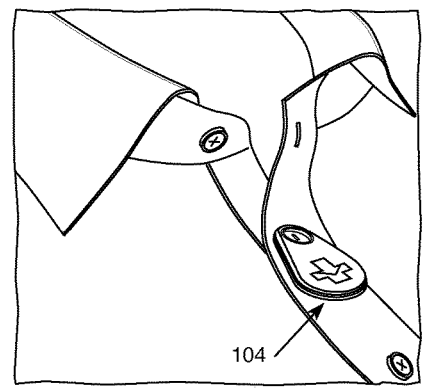
FIG. 4 illustrates one location where the wearable disease prevention device of FIG. 1 can be attached on a user.
Figure 5:
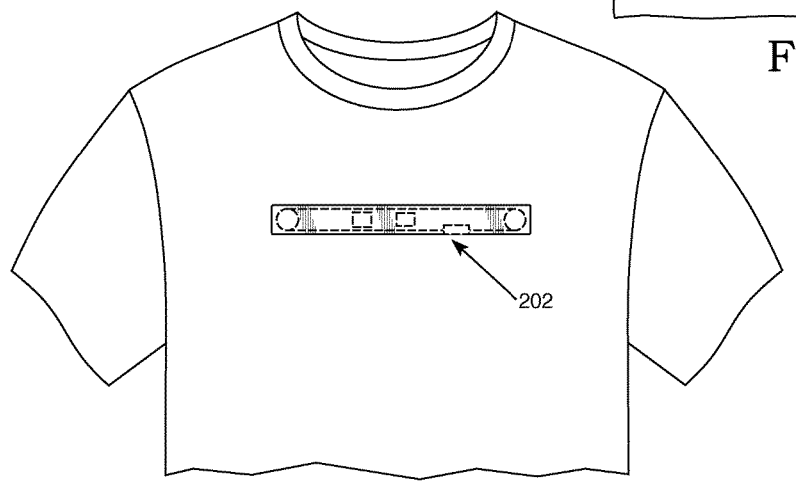
FIG. 5 illustrates one location where the wearable disease prevention device of FIG. 2 can be attached on a user.

FIGS. 1-5 illustrate examples of the wearable device. FIG. 1 illustrates various components of a first embodiment of the disclosed wearable disease prevention device, such as a cradle 102, an emitter/detector 104 that fits in the cradle, and rings 106 to be worn on a user's hands. FIG. 2 illustrates various components of a second embodiment of the disclosed wearable disease prevention device, such as a housing 202, a backer 204, magnets 206 to attach the backer to the housing, a signal emitter 208, a plurality of sensors 210, a micro USB charge port 212, and a power button 214. FIGS. 3-4 illustrate various ways a user can wear the cradle 102 and emitter/detector 104 of the first embodiment of the wearable disease prevention device. FIG. 5 illustrates one way a user can wear the second embodiment of the wearable disease prevention device. While comparative sizes are illustrated in the drawings, the size of the wearable disease prevent device can vary and are not specific to the sizes illustrated.

As illustrated in FIG. 1, a first embodiment 100 of the disease prevention device includes a cradle 102, an emitter/detector 104 that can fit in the cradle, and one or more rings 106. The cradle can have a solid backing 108, walls 110, and an open front face. The walls 110 can surround all sides of the cradle 102, or they can be limited to a specific area, such as a top and bottom, as illustrated in FIG. 1. The emitter/detector 104 can have a similar shape to the cradle 102 (for example, a tear drop shape) and, therefore, fit snuggly in the cradle 102 when inserted. Alternatively, the emitter/detector 104 can operate independently from the cradle 102.

In some embodiments, a portion of the emitter/detector 104 will hang over one or more edges of the solid backing 108 so a user can easily remove the emitter/detector 104 from the cradle 102. This may be useful if a user has to change the battery or if a different cradle 102 is desired. Additionally, some cradles 102 may have a clip 112 on their back so a user can clip the cradle 102 and attached emitter/detector 104 to a piece of clothing or accessory, as illustrated in FIG. 3. In some embodiments, the emitter/detector 104 can attach directly to a button, as illustrated in FIG. 4, and no cradle 102 is needed. More specifically, the emitter/detector 104 can have an aperture 114 that slides over and around a button. In addition to the aperture 114, the emitter/detector 104 can have a sensor 116 on its front that faces away from the wearer, as illustrated in FIGS. 3 and 4.

As illustrated in FIG. 2, a second embodiment 200 of the disease prevention device includes a housing 202, a backer 204, magnets 206 to attach the backer to the housing, a signal emitter 208, a plurality of sensors 210, a micro USB charge port 212, and a power button 214. The housing 202 can be elongated in that it can be relatively rectangular having long edges along the top and bottom of the device and the short edges along the left and right ends of the device. Additionally the housing 202 can have a relatively flat front face, back face, or both. The backer 204 can also be elongated in shape having long edges along its top and bottom, short edges along its right and left ends, and a relatively flat front face, back face, or both. The right and left ends of the housing 202 and/or the backer 204 may, instead of being squared off, be rounded. The right and left (i.e., first and second) ends of the backer 204 can each be attached to a magnet 206. Alternatively, the backer 204 may be two separate pieces with each piece having a magnet 206.

In a preferred embodiment, the housing 202 can be a flexible board that houses the signal emitter 208, the plurality of sensors 210, the micro USB charge port 212, and the power button 214, as illustrated in FIG. 2. However, any or all of these components may also be housed on the backer 204. While the housing 202 is a board preferably made of a flexible material to prevent snapping or breaking, it can also be rigid. The signal emitter 208 is preferably located near the center of the housing 202 in order to emit equally to both sides of a wearer's face. The plurality of sensors 210 are preferably located on the right and left ends of the housing 202. This enables the device to have a wide detection zone (i.e., it can pick up face touching on either side of the face) and to determine which side of the face the user may be about to touch or currently touching. The micro USB charge port 212 and power button 214 may be located at other locations along the housing 202 away from the center or ends so as not to interfere with the signal emitter 208 and sensor 210.

Figure 6:
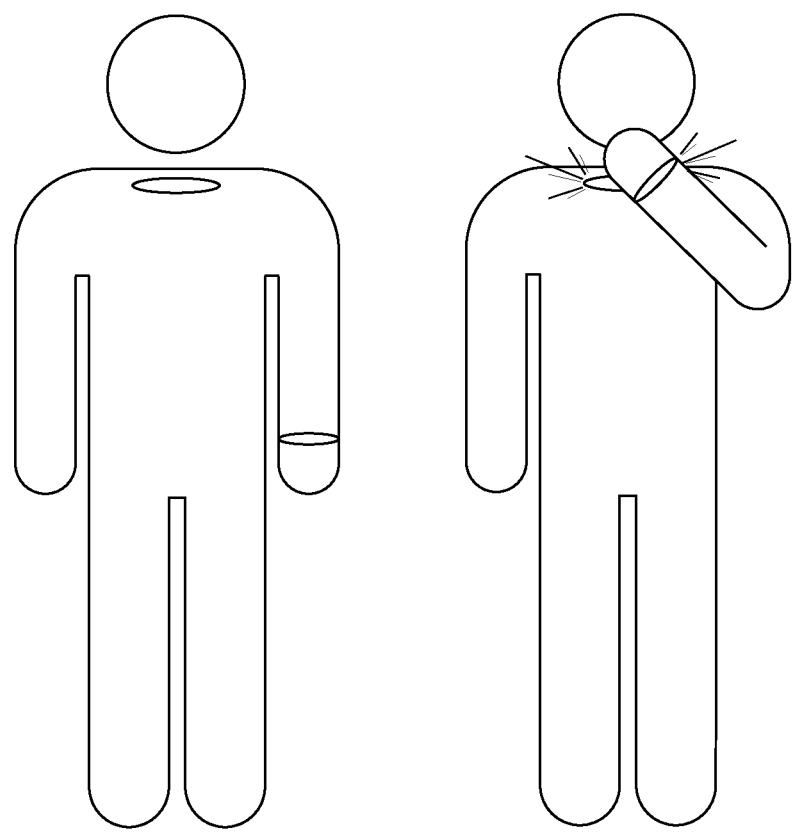
FIG. 6 illustrates activation of the alert when a user's hand is in close proximity to the user's face.

The housing 202 and/or backer 204 may also provide instant feedback of face touching, or potential face touching, to a user by incorporating a vibration component or an auditory component that is activated when a user has touched, or is about to touch, his or her face, as illustrated in FIG. 6. For example, the signal emitter 208 may emit a light wave that bounces off of the user's hand or forearm and is picked up by a sensor 210. The sensor 210 that picks up the signal may then transmit this information and cause the vibration component or auditory component to activate, thereby informing the user that his or her hand is near his or her face.

Generally, while the location of the disease prevention device is critical, it can be worn on a wearer's shirt or other location near the wearer's face, as illustrated in FIGS. 3-5. In some embodiments, the device can work alone and can detect a user's hand or forearm when the hand or forearm is in a position to indicate face touching. In another embodiment, the device can work in tandem with reflective wristbands worn by the user on each of his or her wrists. Most importantly, the device, when worn by the user, should be located high enough on a user's chest that is not accidentally tripped by irrelevant hand or forearm movement that occurs away from a user's face. It should also be low enough so that a user does not accidentally bump the device with his or her face.

In some embodiments, the device may be part of a wearer's clothing (for example, a button) or may be removably connected to a wearer's clothing. In another embodiment, the disease prevention device is mounted to or incorporated onto or into a device. For example, the device may mount to a computer monitor or may be built into the computer camera. Regardless of where the device is located when it is separate from the user, it can face the user when the user is operating the device and can, therefore, accurately detect face touching.

The device may have an infrared (IR) emitter and an IR detector and can, therefore transmit and receive IR signals. In another embodiment, the device uses a different form of motion detection or uses radiofrequency (for example, if the device was hidden underneath clothing) to emit and detect signals.

In use, the device can constantly or intermittently (for example, using a pulse) transmit a signal, detect the signal when it bounces off of an object, such as a wearer's hand or a reflective wristband, back toward the device, and alert the wearer that it has detected the signal using tactical or auditory alerts on the device itself or by syncing to a mobile device and causing the mobile device to alert the user. The signal preferably emits from the emitter 104 or signal emitter 208 in a specific pattern or with a specific strength that the detector 104 or sensor 210 on the device can detect. A specific pattern can prevent accidental detections (i.e., false positives) by, for example, preventing the device from being triggered by other sources of light or by sunlight, which emit at constant rates. A signal emitting at a specific strength allows the sensitivity of the detector 104 or sensor 210 to be adjusted so it is sensitive enough to pick up the signal from the emitter 104 or signal emitter 208 but not so sensitive that gesticulations or other hand movements near the face will trigger a detection. In one embodiment, the emitter 104 or 208 produces approximately a 940 nm light frequency, although it can emit between 720 nm and 1720 nm. In a further embodiment, the detector 104 or sensor 210 can recognize an ordinary object (for example, a hand or forearm) from two to eight inches away that is reflecting or emitting a light within the 720 nm to 1720 nm frequency. In the case where reflective wrist bands are used, the detection distance is tripled, which enables the detection sensitivity of the detector 104 or sensor 210 to be very low. This beneficially avoids false trips from unintended objects.

Additionally, the detector may only detect within a specific field. For example, the field range or detection zone may be 120 degrees wide, 20 degrees tall, and may detect within a distance of a few inches. In some embodiments, the detection zone can be adjusted. Preferably, the detection zone is wide and, therefore, in some embodiments, the disease prevention device may have two motion-based sensors 210 on opposite ends of an elongated housing that stretches left to right, as illustrated in FIG. 2. An added benefit is that if one of the two sensors 210 is triggered, it can indicate the specific side of the face the user is touching. However, the disease prevention device does not require two sensors 210 and, therefore, one sensor 210 having a wide detection beam may also be utilized.

Therefore, when the device detects the deflected signal within a predetermined range, it can send an output signal to an alert function, such as an audio feature that will, for example, emit a beep, chirp, vibration, or other alert noise. It can additionally, or alternatively, send an output signal to a computing device, such as a desktop, laptop, or mobile device, to record the event.

In some embodiments, other methods of detection are used. For example, proximity detection may occur by radio frequency, magnetism, capacitance, inductance, resistance, accelerometers, optical (signal pattern or color), or some combination of the above. Additionally, locations of the emitter/detector 104 and sensor 210 include the neck, a collar, a button lapel, upper chest (as described in more detail above), eyeglasses, earrings, etc. Locations of the reflective object, if used, can include the hands, fingers, wrists, over the top of bracelets, over the top of other hand jewelry, etc. Alternatively, the reflective objects may be the objects, such as reflective bracelets, reflective wristbands, reflective rings, etc. instead of being located on objects.

Regardless of the method of detection, when the device does detect that a user's hand is in close proximity to the user's face, the device can modify the user's behavior by instant feedback. For example, the device can emit beeps, chirps, other audio signals, vibrations, or a visible light signal to alert users that they are either close to touching their faces, are touching their faces, or have recently touched their faces. Additionally, or alternatively, the device can communicate this detection to a mobile device, which can alert users of the close physical proximity of their hands to their faces by emitting a noise, light, vibration, etc.

Figure 7:
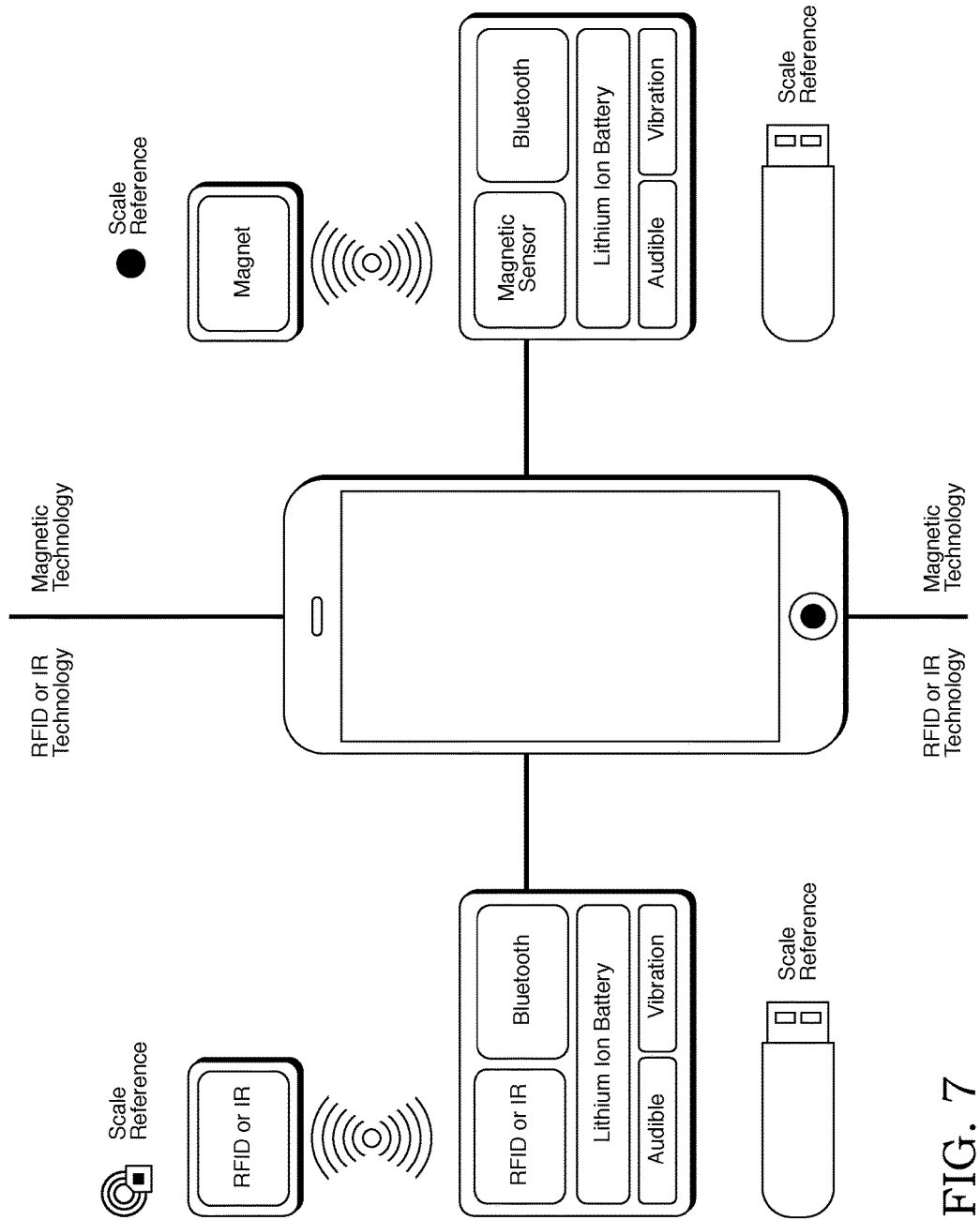
FIG. 7 illustrates two types of technology that may be used in accordance with the below-described wearable disease prevention device.
Figure 9:
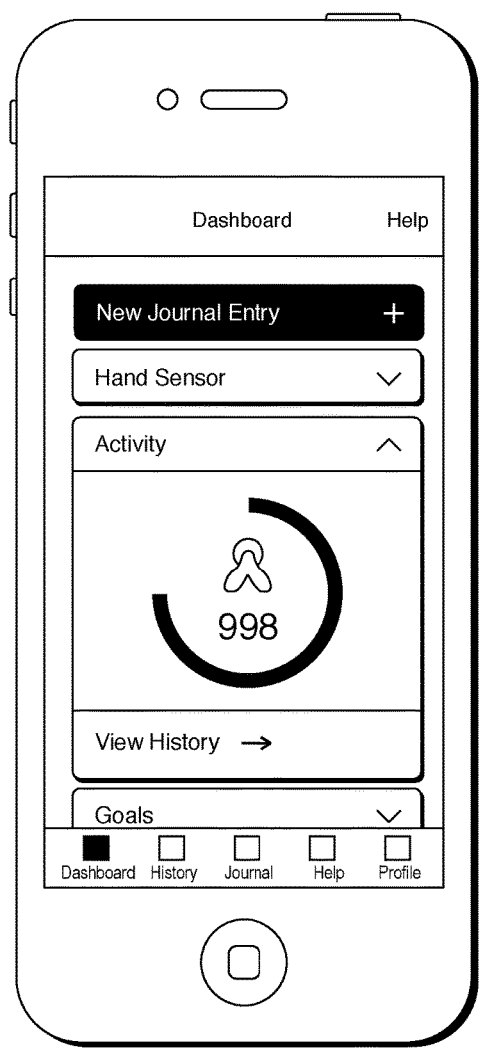
FIG. 9 is an example graphical user interface showing a mobile interface activity-tracking screen according to one embodiment of the present invention.

When the device detects the signal, indicating that the user's hand, forearm, or reflective object is close to the device, it can, in addition to warning the user, send timestamp or other data to a software application via Bluetooth or Wi-Fi signal, as illustrated in FIG. 7. The software application can then capture the data, store it, analyze it, and present it graphically or categorically to the user, as illustrated in FIG. 9, to inform the user of his or her facial touching habits. For example, the user can be made aware of the number of times per day the user is touching his or her face, when the user's behavior is the most common, how the user's behavior is changing, what improvements or regressions in behavior have occurred, etc. This information can help the user understand and avoid certain triggers. In some embodiments, the software can help the user set goals and generate motivations to encourage self-improvement. By being more aware of current habits, the user can modify his or her behavior to reduce facial touching and, therefore, prevent the spread of disease.

To implement the above-described features, a third embodiment of the disclosed wearable disease prevention device can be comprised of a light (such as infrared) emitter, a light detector, a field of view limiting shroud slot, and various user selectable shrouds to fit the field of view limiting shroud slot. Any of the above-described embodiments may also have, in addition to the features previously mentioned, an adjustable control to reduce detection sensitivity and distance, an light controller chip to encode and decode a unique light signal/sequence, a rechargeable battery with a predetermined battery life of 0.5 to 2.0 watt hours, a smartcharge circuit, a USB port for charging the battery (ex: a micro USB-B port), and a power switch to turn the device on and off.

As mentioned above, the device can be used in combination with reflective wristbands. However, the device can also be used in combination with pre-existing reflective objects, such as metallic bracelets, or specially created reflective objects, such as reflective surgical gloves for doctors. For example, the surgical gloves can be reflective in their entirety or they can have reflective pieces incorporated throughout. To set up a baseline parameter for the detector's field of view, a user can move the reflective wristband into various positions relative to the user's face and can alter the device's settings so that it only has the potential of activating in areas or regions that the user selects.

More specifically, some electrical features may include: a pulsed light generator (110 degree angle), a sensor paired to match the pulsed light generator, and a low current draw to extend the battery life (for example, to two or more days). In some embodiments, the light emitter can be a wide-angle light emitter, and the sensor can be a wide-angle light detector. The user selectable shrouds, if used, are used to limit the light detector's field of view for various detection zones.

In a preferred embodiment, as described above, at least a portion of the device is magnetized and has a housing 202 and a backer 204 so the device can be magnetically adhered near the upper chest of a user, as illustrated in FIG. 5. In another embodiment, the device has a compact design so it can easily be worn on a user's shirt button, as illustrated in FIG. 4, or otherwise attached to a user's clothing. For example, it may be clipped onto a collar or near the neck opening of a shirt, as illustrated in FIG. 3, it may wrap around a user's button, it may hook onto a user's button, it may hang on a necklace-type feature that itself hangs around a user's neck, or it may take the form of a pendant and be pinned to a user's shirt. The device can also be waterproof and resistant to dropping and/or smashing.

In some embodiments, the disease prevention device can be further comprised of a Bluetooth transmitter that can pair with, and transmit to, a mobile device having a mobile application used for diagnosing, tracking, and training individuals' face-touching habits. Therefore, the device and the reflective objects can be used in combination with a mobile application that is designed to receive touch events from the Bluetooth transmitter, to log the events, and, if desired, to either beep or vibrate the device when an event has occurred. However, a Bluetooth transmitter is not necessary. An alternative embodiment can, instead, include an alert function on the device itself, such as a vibration feature or a speaker that is triggered after the light signal/sequence is detected to emit a beep or chirp.

The mobile application can be used as a diagnostic and assessment tool to treat the user. For example, it can complete tasks such as logging events (for example, detections of face touches), with a timestamp, displaying a log of the timestamps in graphical form, activating a vibration feature in the mobile device when a detection occurs, and/or activating an alert (auditory, physical, or visual) feature in the mobile device when a detection occurs.

If the alert is auditory, for example, a beep, the beeping can be one beep or chirp or repetitive beeps or chirps that occur the entire time the light signal is detected. In the case of repetitive beeps or chirps, the frequency of beeping/chirping can be selectable. If the alert is physical, the mobile device can vibrate once, repetitively, or consistently while the light signal is detected. If the alert is visual, the mobile device can light up once, repetitively, or consistently while the light signal is detected. Other alerts that could occur are messages sent through the mobile application to the user's messaging or texting function. In addition to logging occasions of face touching, the mobile application can evaluate infection rates and determine if they are correlated with face touching frequency.

In some embodiments, instead of reflective wristbands, the user may have one or more rings, as illustrated in FIG. 1, each one with an RFID tag embedded. Therefore, when the ring or rings come into close proximity with the device, which is detecting radio frequency, the device can detect the RF signal and emit a beep, chirp, or vibration, or it can send a signal to a mobile device.

In some embodiments, where there is an audio feature to emit a beep or chirp directly from the disease prevention device, the audio feature can contain a frequency range desirable for the wearer. For example, the audio frequency may be selected to operate in a frequency that does interfere with hearing aids and that, therefore, does not irritate elderly adults or other individuals with hearing aids. In another example, if the device is used to train certain behavior in dogs or other pets, the audio frequency may be higher than the human range so as not to irritate any humans.

The above-described device helps prevent people from touching their faces and, therefore, prevents the spread of disease. It can be beneficial for health conscious individuals, such as doctors, nurses, daycare workers, teachers, and individuals with compromised immune systems, and it can be beneficial for health conscious businesses, such as hospitals, daycares, schools, and nursing homes. It can also be beneficial for acne sufferers, nail biters, nose pickers, thumbsuckers, eye rubbers, and makeup wearers.

Figure 8:
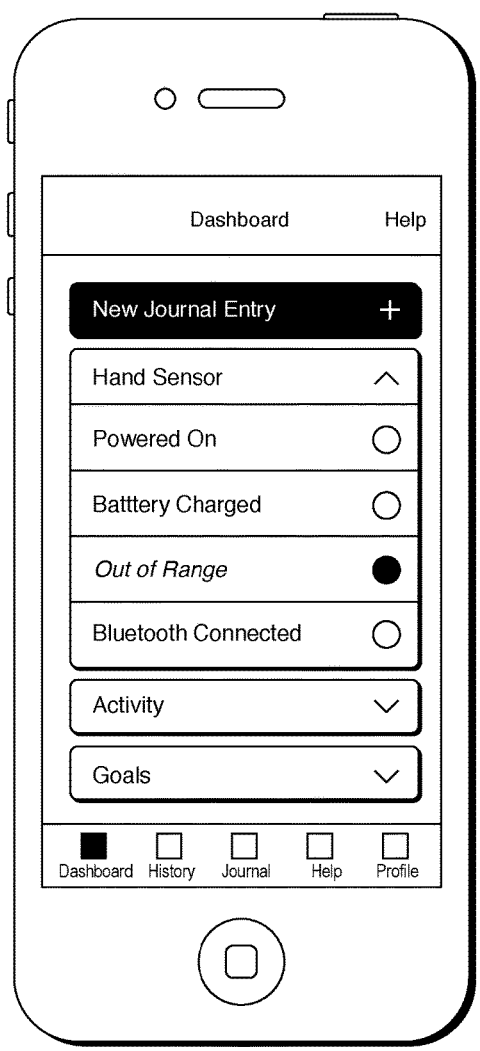
FIG. 8 is an example graphical user interface showing a mobile interface device-tracking screen according to one embodiment of the present invention.

In one example scenario, a new user purchases the device, which is comprised of two sensors, a central sensor having the emitter/detector and a floating sensor that reflects a signal. The user configures the physical components, verifies that the sensors are adequately charged, attaches the central sensor to an area close to his or her neck, and then attaches the floating sensor to his or her hand. The user then downloads the mobile application to support communication and data acquisition with the supporting sensors. Upon installing the mobile application, the user is prompted to login or create a new account. The user then pairs the two sensors with the mobile application to allow effective communication with the mobile application and to allow access to product features. If, as illustrated in FIG. 8, the mobile device that hosts the mobile application is out of range, the application may indicate as much.

Upon set-up, the user is prompted to select the "habit-event" that he or she would like to log, which ultimately results in use of the tools within the system to deter and retrain behaviors in order to reduce unwanted behaviors. Upon opening the mobile application, the mobile application prompts the user through a personal wizard that allows the user to personalize the mobile application and data reporting. The mobile application features begin with an assessment and evaluation, which suggests the user track and record habit-events for 24 hours.

Prior to launching the assessment, the mobile application provides the user with a questionnaire to create a baseline of information for the user. Following the user's assessment, the results are shared with the user and compared to the questionnaire, and the user is asked if he or she wants to utilize the product mobile application to achieve his or her goals.

The mobile application defaults to tier-based steps that establish goals of habit reductions over an eight-week period. For example, tier one may take place from week 1 to week 3 and promote a 25% reduction, tier two may take place form week 3 to week 5 and promote a 40% overall reduction, and tier three may take place from week 5 to week 8 and promote a 65% overall reduction. However, the program is customizable.

In addition to setting up the program, a user can select a desired level of awareness, instruction, and correction. For example, "low" levels may provide some awareness, instruction, and correction; "medium" levels may provide moderate awareness, instruction, and correction; and "high" levels may produce strict awareness, instruction, and correction. In some embodiments, improvements can be tracked on social media and the process of improvement can become competitive.

The various embodiments described above are provided by way of illustration only and should not be construed to limit the claims attached hereto. Those skilled in the art will readily recognize various modifications and changes that may be made without following the example embodiments and applications illustrated and described herein and without departing from the true spirit and scope of the following claims.

What is claimed is:
1. A wearable disease prevention device comprising:
   a housing;
   a backer structured and configured to attach to the housing;
   a plurality of signal emitters;
   a plurality of sensors enabled to detect when a wearer's hand is near a wearer's face; and
   at least one reflective wristband configured to reflect a signal from at least one of the plurality of signal emitters back to at least one of the plurality of sensors;
   wherein:
      a first of the plurality of sensors is enabled to detect when the wearer's left hand is near the wearer's face, and
      a second of the plurality of sensors is enabled to detect when the wearer's right hand is near the wearer's face.
2. The wearable disease prevention device of claim 1, wherein:
   the housing is comprised of a flexible board;
   a front of the housing is relatively flat;
   a back of the housing is relatively flat; and
   a top edge and a bottom edge of the housing have a longer length than a left edge and a right edge.
3. The wearable disease prevention device of claim 2, wherein:
   a front of the backer is relatively flat;
   a back of the backer is relatively flat; and
   a top edge and a bottom edge of the backer have a longer length than a left edge and a right edge.

4. The wearable disease prevention device of claim 3, wherein the left edge and the right edge of the backer are rounded.

5. The wearable disease prevention device of claim 3, wherein the left edge and the right edge of the backer can each be attached to one of the plurality of magnets.

6. The wearable disease prevention device of claim 1, wherein the housing houses the plurality of signal emitters, the plurality of sensors, and the power button.

7. The wearable disease prevention device of claim 6, wherein:
   the housing houses the plurality of signal emitters near a center of the housing,
   a first of the plurality of sensors near a left edge of the housing, and
   a second of the plurality of sensors near a right edge of the housing.

8. The wearable disease prevention device of claim 6, wherein the housing provides instant feedback to the wearer when the wearer's hand is near the wearer's face.

9. The wearable disease prevention device of claim 8, wherein the instant feedback is in the form of a physical alert, an auditory alert, a visual alert, or combinations thereof.

10. The wearable disease prevention device of claim 1, further comprising a plurality of magnets, wherein:
    the housing is elongated; and
    the plurality of magnets are structured and configured to attach the backer to the housing.

11. The wearable disease prevention device of claim 1, further comprising a micro USB charge port and a power button.

12. A method for preventing the spread of disease, the method comprising:
    detecting a potential face-touching event when a wearer's hand comes into proximity of the wearer's face;
    alerting the wearer instantly of the potential face-touching event via an alert module;
    communicating the potential face-touching event to a mobile device;
    tracking date and time data related to the potential face-touching event; and
    reporting date and time data related to the potential face-touching event
    wherein:
      a wearable device located on the wearer's chest is comprised of a housing, a signal emitter, and a plurality of sensors;
      the signal emitter emits a light wave that reflects off of the wearer's forearm;
      the reflected light wave is detected by the sensor; and
      the sensor transmits confirmed detection to the alert module.

13. The method of claim 12, wherein the alert module is selected from the group consisting of a physical alert, an auditory alert, a visual alert, and combinations thereof.

14. A wearable disease prevention device comprising:
    a cradle having a solid backing, a top wall, a bottom wall, an open front face, and a clip attached to the solid backing;
    an emitter/detector that fits in the cradle and is comprised of:
      an infrared emitter that emits an infrared signal;
      an infrared detector enabled to detect when a wearer's hand is near the wearer's face;
      a USB charge port for charging a rechargeable battery;
      a power switch to turn the device on and off; and
      an aperture enabled to attach directly to a shirt button;
    a Bluetooth transmitter that can pair with, and transmit to, a mobile application on a mobile device; and
    one or more rings;
    wherein the mobile application is configured to:
      receive a potential face-touching event notice from the Bluetooth transmitter;
      track date and time data related to the potential face-touching event; and
      report date and time data related to the potential face-touching event.

15. The wearable disease prevention device of claim 14, wherein the cradle and the emitter/detector have a tear drop shape.

16. The wearable disease prevention device of claim 14, further comprising:
    an infrared controller chip to encode and decode a unique infrared signal, wherein the infrared emitter emits the unique infrared signal and the infrared detector detects the unique infrared signal;
    an adjustable control to reduce detection sensitivity and distance; and
    a smartcharge circuit.

17. The wearable disease prevention device of claim 16, wherein the infrared detector is enabled to alert a user of the detected unique infrared signal.

18. The wearable disease prevention device of claim 17, wherein:
    the Bluetooth transmitter transmits a data package to the mobile application that includes data related to the detected signal; and
    the mobile application timestamps and analyzes the data package.

* * * * *